United States Patent [19]

Ozawa

[11] Patent Number: 4,912,365
[45] Date of Patent: Mar. 27, 1990

[54] AUTOMATIC CARBON-REPLACING WEATHER RESISTANCE TESTING APPARATUS

[75] Inventor: Hiroshi Ozawa, Tokyo, Japan
[73] Assignee: Suga Test Instruments Co., Ltd., Tokyo, Japan
[21] Appl. No.: 299,566
[22] Filed: Jan. 18, 1989
[51] Int. Cl.$^4$ ............................................. H05B 31/20
[52] U.S. Cl. ........................................ 314/1; 314/5; 362/264
[58] Field of Search ........................................ 314/1-6, 314/35, 51-56, 59, 101; 313/237, 237.71, 236; 362/261, 262

[56] References Cited

U.S. PATENT DOCUMENTS

| | | | |
|---|---|---|---|
| 679,878 | 8/1901 | Bremer | 362/261 |
| 2,151,745 | 3/1939 | Coates | 314/8 |
| 3,409,795 | 11/1968 | Lauxen et al. | 314/6 |

Primary Examiner—Roy N. Envall, Jr.
Attorney, Agent, or Firm—Wenderoth, Lind & Ponack

[57] ABSTRACT

A carbon exchanging system for a carbon-arc weather resistance testing apparatus having a carbon drive system including a reversible motor for automatically moving upper and lower arc producing carbons toward and away from each other along a vertical line for keeping the discharge current and voltage substantially constant. The carbon exchanging system has remotely operable upper and lower carbon chucks for holding the upper and lower carbons, a carbon replacing device having a remotely operable exchanging chuck and a drive for moving the exchanging chuck along a path of movement toward and away from the upper and lower carbon chucks when they are in position on the vertical line, a shifting device for shifting the carbon drive system and the carbon replacing means relative to each other for moving the upper and lower chucks and the exchanging chuck laterally relative to the vertical line, a carbon supply adjacent the path of movement of the exchanging chuck for holding replacement carbons and moving them into position opposite a position of the exchanging chuck along the path, and a moving device for moving the exchanging chuck and the carbon supply relative to each other in a direction toward and away from each other. The system can also include a control device for automatically controlling the operation thereof.

9 Claims, 4 Drawing Sheets

AUTOMATIC CARBON-REPLACING WEATHER RESISTANCE TESTING APPARATUS

The present invention relates to a weather resistance testing apparatus in which a material is subjected to accelerated aging by artificially producing, with the use of an artificial light source that takes the place of the sun, weather conditions simulating an outdoor environment in which the material is exposed to the sun's rays, rain, wind, outside temperatures and relative humidity.

In a conventional weather resistance testing apparatus, as shown in FIG. 6, a light source is centered in a test chamber, and specimen turning frames turn around the light source with specimens mounted therein. In addition, spray nozzles (not shown) which reproduce the phenoma of rainfall are provided for intermittently spraying the specimens with drops of water.

In this way, weathering is performed by the irradiation of light and simulation of rainfall. A carbon-arc or xenon lamp is used as the artificial light source.

A representative example of the carbon-arc lamp weather meter is described in JIS B-7753 "Sunshine Carbon-Arc Lamp Weather Meter". In this light source, which comprises four pairs of upper and lower carbons, discharge takes place between the carbons of any one of the pairs and transfers to another pair of the carbons as the carbons are consumed. The maximum lighting time is 60 hours.

The discharge transfers from one pair of carbons to another pair of carbons in the manner described below.

The four upper and lower carbons of the four pairs are respectively provided on spaced opposed mounts, and the two mounts are simultaneously moved toward each other in the vertical direction by a reversible motor 5. A current flows between the carbons and is maintained at a normal value of 60A during the discharge. However, when the ends of the carbons are consumed and the distance between the upper and lower ends is increased, the current is reduced.

When the current becomes less than 60A, the reversible motor is operated to move the upper and lower carbons so that the distance therebetween is decreased. In addition, at the start of discharge, if a current is supplied to the carbons when the ends of all four pairs of carbons are only close to each other but not touching, no current flows because discharge is not taking place between the upper and lower carbons, and the reversible motor is operated to cause the upper and lower carbons to approach each other. When the ends of any one of the pairs of carbons are brought into contact with each other, a short-circuit current (about 80A) flows through the touching carbons. Since the current exceeds 60A, the reversible motor is adapted to rotate reversely, and the ends of the carbons are separated from each other the moment this short-circuiting occurs. Therefore, the short-circuited state is changed to the discharge (arc) state and the current is reduced by the separation of the carbons, and is thus automatically kept at 60A. When the carbon pair between which discharge is occuring is consumed and as a result the distance between these carbons is increased, they are brought closer to each other by the operation of the reversible motor. However, if a second pair of carbons is brought into contact with each other before the current through the first pair reaches 60A, a current flows through the second pair of carbons, and the discharge between the first pair of carbons ceases and is transferred to the second pair of carbons. Since the discharge is instantaneously and smoothly transferred, a constant discharge is maintained to serve as a light source until all four pairs of carbons can no longer continue the discharge. This provides a service life of about 60 hours. The carbons that are shortened after being consumed by the discharge are replaced by new ones, and lighting is again performed and continues for another 60 hours, so that specimens can be continuously tested over a long period.

A xenon lamp provides continuous lighting for 2000 hours, but it has disadvantages in that the energy level is reduced during the course of its use and thus lacks the ability to provide a light source for weathering tests which maintains a constant level of irradiation energy. In contrast, because the carbons in a carbon-arc lamp are always replaced by new ones and the discharge current and voltage are controlled at a given value, this has the advantage that a constant level of irradiation energy can be consistently obtained.

However, although the carbon-arc lamp can satisfy the most fundamental requirement for a weather resistance testing apparatus, it has a disadvantage in that carbons must be replaced with new ones owing to the steady consumption of carbon, which causes interruptions in the light produced thereby. Since arc discharge is produced at high temperatures, the arc lamp itself is very hot immediately after discharge, and thus carbons cannot be replaced immediately after they have been consumed and are no longer useful. A cooling time of one hour or more is required before a change can be made, and thus it is inevitable that tests are interrupted to allow time for cooling and replacing the consumed carbons with new ones. In addition, since the time when the carbon has to be replaced sometimes falls on a holiday or at night, the work of replacing the carbons is a great burden on the operator of a weather resistance testing apparatus.

OBJECT AND BRIEF SUMMARY OF THE INVENTION

It is an object of the present invention to provide an apparatus which overcomes the disadvantages of a conventional carbon-arc type weather resistance testing apparatus by automating the job of replacing carbons.

To this end, there is provided an automatic carbon-replacing weather resistance testing apparatus which makes possible continuous operation by means of automatic replacement of carbons, without the need for manual intervention.

The apparatus according to the invention has only one pair of upper and lower carbons across which discharge occurs, and a plurality of spare carbons are separately provided outside of the discharge chamber, so that when the first carbon pair is consumed by the discharge, the current passing therebetween is automatically cut off, unburnt parts of the carbons are removed, a new pair of upper and lower carbons is mounted in place of the consumed carbons, and the distance between the ends of the replacement upper and lower carbons is automatically adjusted to an appropriate value so that the ends are brought into contact with each other and a current again automatically flows therethrough. The positions of the upper and lower carbons are then adjusted in a conventional way.

The automatic current cutoff, removal of the unburnt carbon ends and placing them in a collection box, mounting of new carbons, adjustment of the distance between the carbon ends, and current supplying are automatically performed in sequence within a short period.

An upper carbon chuck for holding the upper carbon and a lower carbon chuck for holding the lower carbon each has a structure by which the carbons can be freely held and removed.

The upper and lower carbon chucks are provided on a carbon drive shaft which is driven by a reversible motor, and are moved toward or away from each other as the reversible motor turns in the forward or reverse direction so that stable discharge can be provided.

This apparatus also provides a carbon supply means in which a large number of replacement carbons are received and held. If an upper carbon is consumed, an exchanging chuck, which is vertically moved by a carbon replacing system, removes the consumed upper carbon held by the upper chuck, returns to the carbon supply means, picks up a replacement upper carbon, and mounts it in the upper carbon chuck.

In a similar manner, the exchanging chuck removes the consumed lower carbon and replaces it with a new one automatically.

The holding and removal of carbons by the exchanging chuck is made possible by a chuck opening and closing system which comprises a moving cylinder and a guide wire which operates in such a way that the guide wire is tightened or loosened by the stroke of the moving cylinder.

Since a series of mechanisms consisting of the carbon drive shaft, the carbon exchange system with the chuck opening and closing system, the carbon supply means, and carbon supply cycle movement device must be operated in cooperation with each other, an electrical control system is provided which controls the operation of these mechanisms.

DETAILED DESCRIPTION AND PREFERRED EMBODIMENTS

Figure 6:
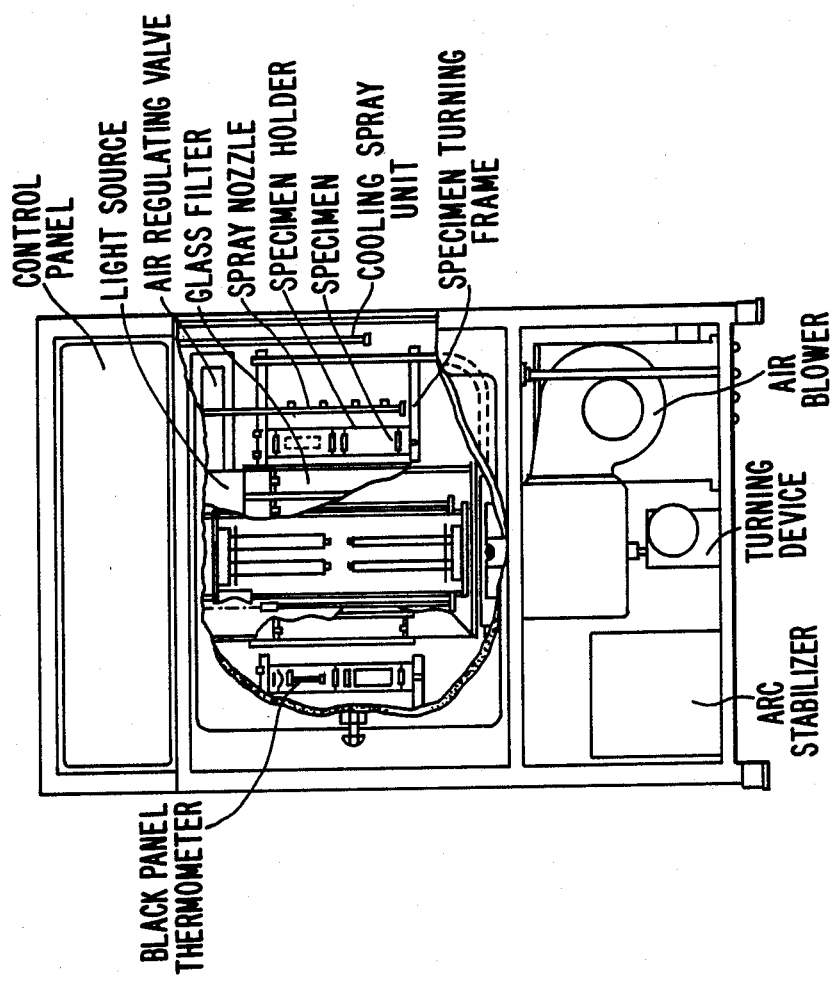
FIG. 6 is an elevation view, partly broken away, of a conventional weather resistance testing apparatus.
Figure 1:
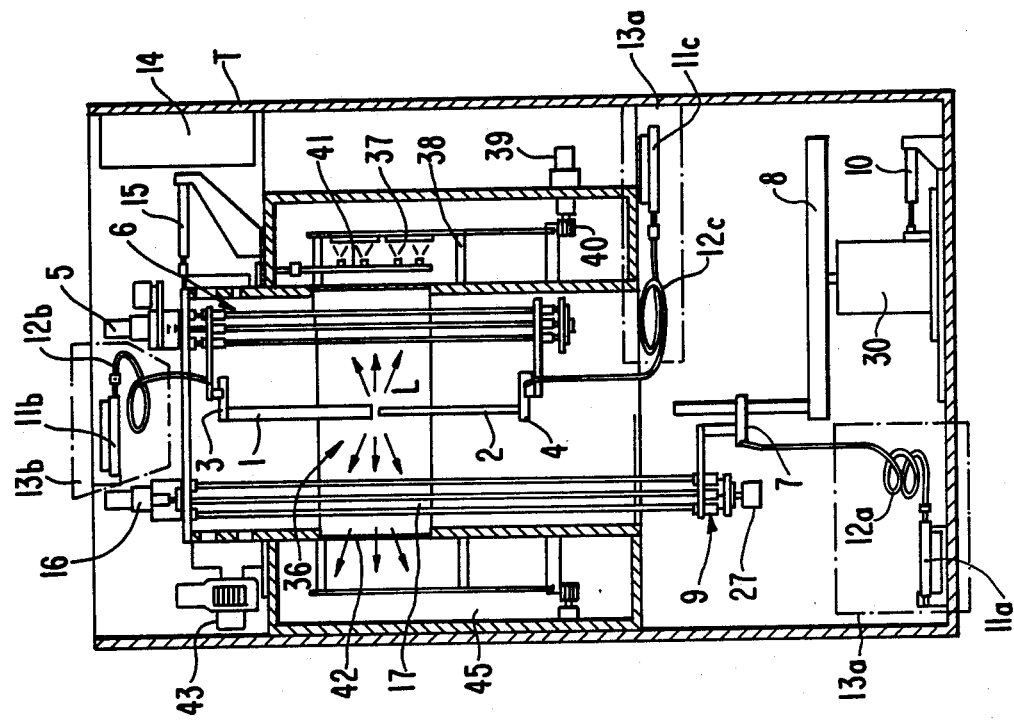
FIG. 1 is an elevation view, partly in section, of a weather resistance testing apparatus according to the invention.

An embodiment of the present invention is shown in FIG. 1 and described in detail below. A light source generally indicated at 36 is placed at the center of a test chamber T, and a specimen turning frame 38 is mounted so as to be able to move specimens 37 along a circumferential path around the light source. The specimen turning frame 38 is turned by a specimen turning frame motor 39 and a specimen turning drive gear 40. Spray nozzles 41 intermittently spray water onto the specimens, serving as an artificial rainfall producing means.

Light (arrows denoted by L in FIG. 1) is generated by discharge between an upper carbon 1 and a lower carbon 2 of a carbon arc lamp, the arc constituting the center of the light source. Upper carbon 1 is held in an upper chuck 3, and lower carbon 2 is held in lower chuck 4. Light with wavelengths of 280 nm or less is intercepted by a glass filter 42, so that the specimens are irradiated with light having characteristics similar to those of sunlight striking the ground. The gases and heat generated by the discharge of the carbons are exhausted to the outside by an exhaust blower 43.

In this way, weathering tests are performed.

A carbon drive system 6 for moving the carbons 1 and 2 toward and away from each other comprises a driving screw 20 and two guide shafts 25 parallel to the driving screw 20 on opposite sides thereof, and the driving screw 20 has an upper screw portion 20a above the middle thereof and a lower screw portion 20b below the middle the threads of which are opposite in direction to the upper screw portion 20a. The carbon drive shaft 6 is provided with an upper chuck moving base 21 and lower chuck moving base 22, each having a threaded hole in which a respective screw portion is engageable and sliding holes in which the two guide shafts slide.

The upper carbon chuck 3 and lower carbon chuck 4 are mounted on the upper chuck moving base 21 and lower chuck moving base 22, respectively.

Figure 3:
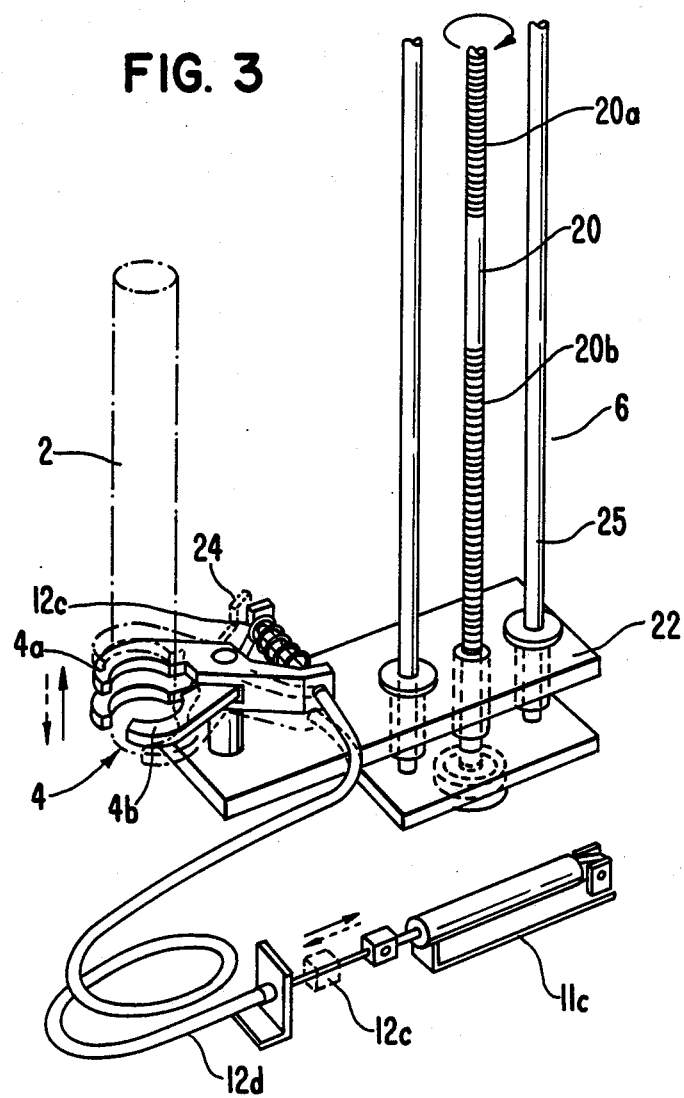
FIG. 3 is a perspective view of a carbon exchanging chuck and a mechanism for the opening and closing of the chuck.

The driving screw is rotated by a reversible motor 5, and when it is rotated in one direction clockwise as indicated in FIG. 3, the upper screw portion 20a moves the upper chuck moving base 21 upward in sliding movement along the guide shafts 25. On the other hand, the lower screw portion moves the lower chuck moving base 22 downward.

If the driving screw 20 is turned in the other direction, counterclockwise as viewed in FIG. 3, by reversing the reversible motor 5, the upper chuck moving base 21 moves downward, and the lower chuck moving base 22 moves upward. Thus, when the reversible motor rotates in one direction, the upper and lower chuck moving bases 21 and 22 move away from each other, so that the upper and lower carbons also move away from each other, while when the reversible motor rotates in the other direction, the upper and lower chuck moving bases 21 and 22 move closer to each other, so that the upper and lower carbons also move closer to each other. By this arrangement, the distance between the ends of the upper and lower carbons 1 and 2 can be freely adjusted by rotation of the reversible motor.

The upper and lower carbon chucks 21 and 22 are each electrically connected to a lighting power transformer 31 by cables, and a current sensing transformer 32 is connected to this circuit so that the voltage generated from the current sensing transformer by the discharge current is converted into a direct current by a rectifier 33. A reference direct-current constant-voltage generator 34 is provided so that a reference voltage generated by this generator 34 is always compared with a direct-current voltage output from the current sensing transformer 32. The direction and magnitude of the current created by the potential difference between the two voltages are amplified by an amplifier 35 and used to turn the reversible motor in one or the other direction. If the potential difference is large, the motor is turned rapidly, and, if it is small, the motor is turned slowly. The amount of movement is substantially in proportion to the value of the potential difference, so that the discharge current flowing between the carbons is always kept at a constant value, e.g. 60A.

This current control system is based on a conventional technique such as that described in U.S. Pat. No. 1,063,346.

A detailed description will now be made of each of the systems used in automatically replacing carbons.

The carbon replacing system 9 comprises a feed screw 17 and two guide shafts 19 which are parallel to the feed screw and on opposite sides thereof, and an exchanging chuck base 18 through which the feed screw 17 extends in threaded engagement and which has sliding holes through which the two guide shafts slide. The base 18 is provided with an exchanging chuck 7, and the moving screw 17 is turned in opposite directions by a carbon-replacing reversible motor 16 so that the exchanging chuck moving base 18 can be moved vertically.

Chuck opening and closing systems 13a, 13b and 13c comprise moving cylinders 11a, 11b and 11c, respectively, and corresponding guide wires 12a, 12b and 12c, which can be Bowdin wires. Air cylinders operated by air pressure, hydraulic cylinders operated by oil pressure, or motor cylinders operated by motors, for example, can be used as the moving cylinders. If air cylinders are used, an air-solenoid valve forming part of the air cylinder structure is opened by a signal from an electrical control system and compressed air from a compressor (not shown) is supplied into the air cylinder so that the movement of a piston in the cylinder is controlled, and the stroke of the piston is adjusted by extending or retracting the piston rod.

The guide wire is connected to the end of the piston rod. The exterior of the guide wire is covered with a flexible protection tube. Each chuck has the same scissor-like structure, which, as shown in FIG. 3, which shows the lower carbon chuck 4, has a fixed carbon-holding portion 4a having two circular claws and a movable portion 4b having a single circular claw and pivoted on the portion 4a between the claws thereof. The portions 4a and 4b are always held open by a spring 24 urging them to pivot away from each other. The guide wire 12c is connected to the movable portion 4b and the protection tube 12d is connected to the fixed portion 4a (FIG. 3).

When the rod of the moving cylinder 11c extended, in the direction shown by the dotted-line arrow, the movable portion 4b is opened. Conversely, when the rod is retracted in the direction shown by the solid-line arrow, the guide wire 12c pivots portion 4b and compresses the spring 24 so as to reduce the opening between the claws, and the chuck is thus closed so as to hold a carbon firmly.

Therefore, a carbon can be held or removed by operating the moving cylinder. This system is provided for each of the upper carbon chuck 3, the lower carbon chuck 4, and the exchanging chuck 7.

If the upper and lower carbon chucks 3 and 4 are moved vertically by the carbon drive system 6, or if the exchanging chuck 7 is moved vertically by the carbon replacing system 9, the flexible guide wires 12a, 12b and 12c can freely follow this movement so that each of the chucks can be opened or closed at any position by the operation of the corresponding moving cylinder.

Figure 5:
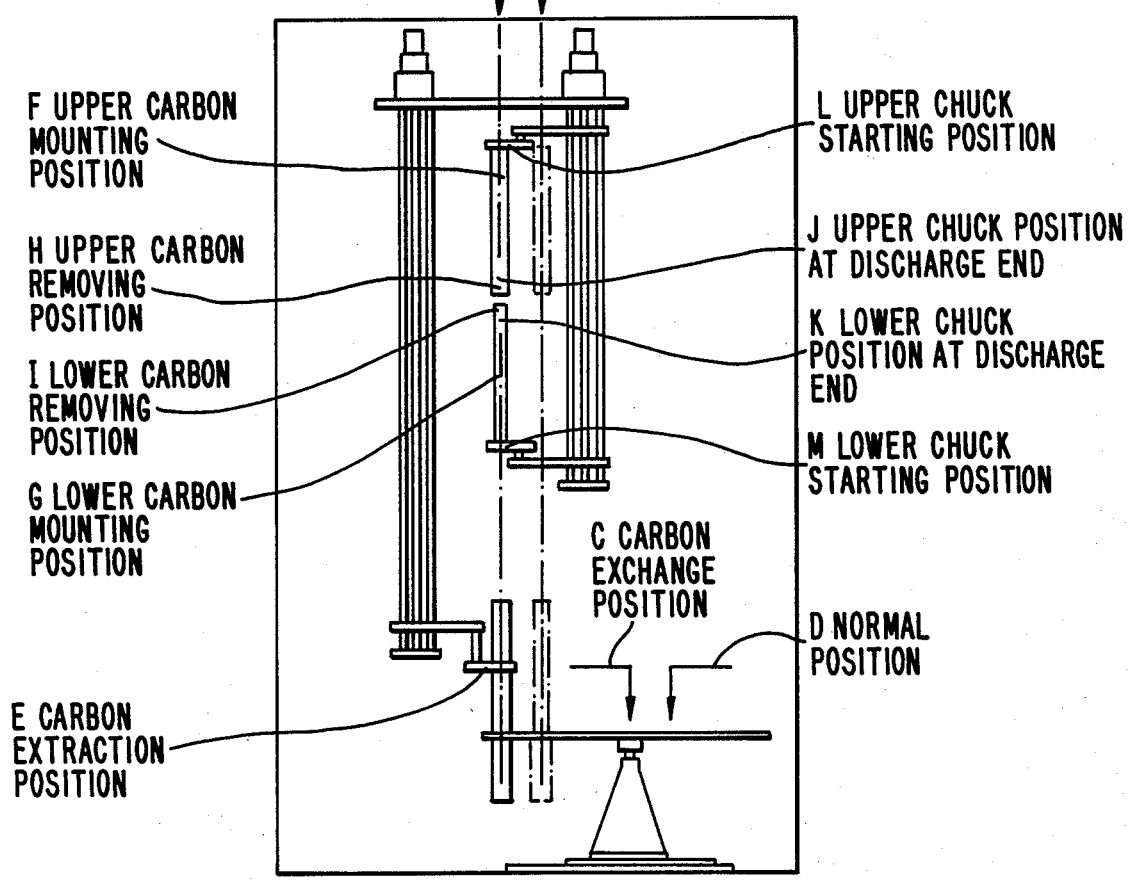
FIG. 5 is a schematic view showing the positions to which the chucks, carbon drive shaft, and carbon supply means move.

The exchanging chuck 7 moves vertically when the carbons are being replaced, and it passes along the center axis A of the light source 36 (see FIG. 5). However, the upper and lower carbon chucks 3 and 4 are also normally on the same center axis, and thus are obstacles to the movement of the exchanging chuck 7. Therefore, a carbon drive system shifting means is provided for moving the upper and lower carbon chucks 3 and 4 away from the center axis when the exchanging chuck 7 is moved vertically by the carbon replacing system 9. The shifting means has a slide base 26 on which the carbon drive system 6 and the reversible motor 5 are mounted and to which a carbon drive system moving unit 15 is connected which is a pneumatic or hydraulic cylinder or the like. The slide base 26 is moved by retracting the rod of the unit 15 so that the upper and lower carbon chucks 3 and 4 are moved to a position B.

The exchanging chuck can be automatically stopped during its vertical movement at level F at which a new upper carbon 1 is to be mounted, a level G at which a new lower carbon 2 is to be mounted, a level H at which a consumed upper carbon is to be removed at the end of discharge, a level I at which a consumed lower carbon is to be removed, a level E at which a new carbon is picked up, and other specific levels, by using an encoder 27 which amplifies and converts the number of revolutions of the feed screw 17 into pulses and which is directly connected to the moving screw 17. The position to which the chuck moving base 18 has been moved downward to its lowest position by the turning of the feed screw 17 is assumed to be a start point, and preset counters which contain setting storage values respectively corresponding to the number of revolution pulses generated while the exchanging chuck travels from the start point up to the levels E, G, I H, or F are provided in the carbon replacing electrical control system 27a. These storage values are each compared with the numbers of pulses generated by the feed screw and sent from the encoder 27, and, if the exchanging chuck is to be stopped at level E, when a setting storage value for level E matches the number of pulses, an instruction is given to stop the reversible motor 16.

Assuming that the number of pulses per revolution is, for example, 32, and the feed per revolution is 5 mm, the exchanging chuck can be stopped to within an accuracy of $\pm 5/32 = 0.16$ mm.

An encoder 27b is connected to the driving screw 20b of the carbon drive shaft through gears 28 and 29 which have the same size, so as to generate pulses corresponding to the number of revolutions of the screw 20b, whereby levels J and K or the upper and lower chucks at which discharge is completed, and start levels L and M of the upper and lower chucks are detected so that the upper and lower chucks can each be stopped at these positions.

The positioning method by use of an encoder is only an example; other position detectors may be used.

Figure 4:
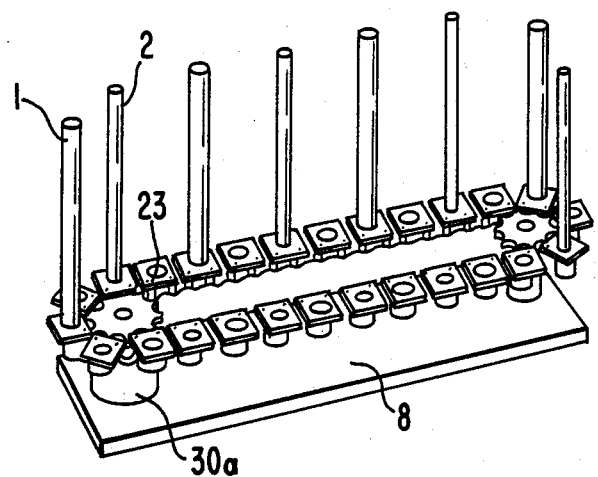
FIG. 4 is a perspective view of an alternative embodiment of a carbon supply means.

A carbon supply means 8 has a rotary annular member 23 on which upper and lower carbons are alternately held upright in holders at predetermined intervals around the periphery. Holders for used carbons are provided in intermediate positions between the holders for the upper and lower carbons or use carbon holders to a position opposite the exchanging chuck 7. A supply means shifting means is provided which is a turning device 30 mounted on a sliding platform 10a which is moved toward and away from the position of the exchanging chuck by a moving means 10 which is a piston-cylinder device like moving device 15. After the turning, the central axis of the carbon supply means is moved to a position D by the moving device 10 so that a replacement carbon is moved into the center of the holding portion of the exchanging chuck 7. As an alternative to the annular member 23, the carbon supply means can have any other equivalent means, such as an endless chain 23a driven by a drive 30a, as shown at 8a in FIG. 4.

The electrical control system 27a generates instructions to actuate the above-described carbon drive system 6, carbon drive system moving unit 15, carbon replacing system 9, carbon supply means 8, carbon supply means movement device 10, upper carbon chuck 3, lower carbon chuck 4, and the chuck opening and shutting systems for the exchanging chuck 7, in cooperation with each other, so that the upper and lower carbons are automatically replaced by new ones in accordance with steps (a) to (U) described below.

A description will now be given of the automatic replacement of carbons in the weather resistance testing apparatus.

(a) Upper carbons 1', 1" and lower carbons 2', 2" are mounted in the holders on the carbon supply means with empty holders left therebetween.

Figure 2:
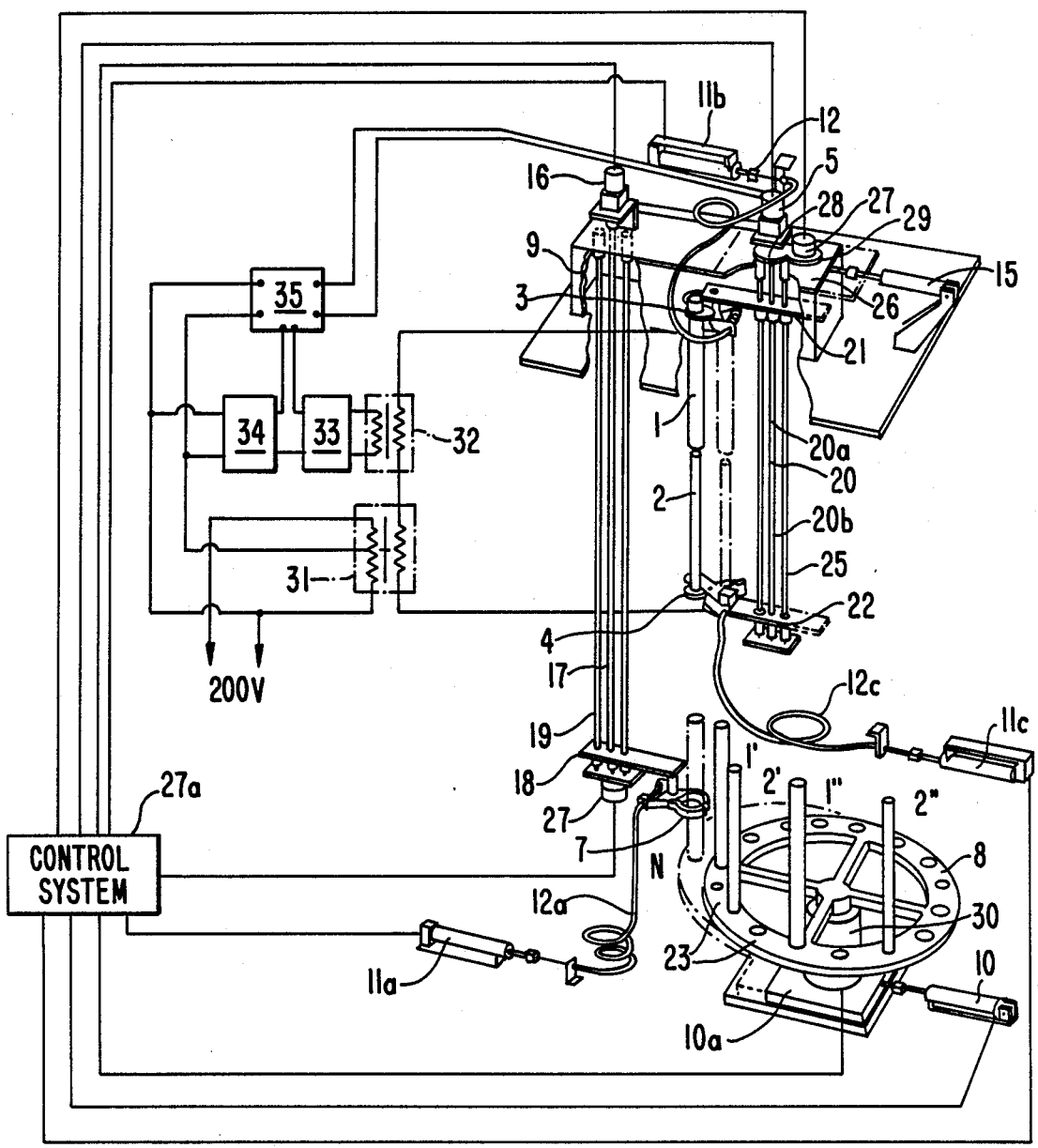
FIG. 2 is a schematic perspective view of part of the apparatus of FIG. 1 for showing the operation of replacing carbons.

(b) The carbon supply means 8 is turned by starting operation thereof from the electrical control system until an upper carbon is moved to a position (denoted by N in FIG. 2) opposite to the exchanging chuck 7.

(c) The feed screw 17 is turned by the operation of the carbon-replacing reversible motor 16 of the carbon replacing system 9 for moving the exchanging chuck moving base 18 vertically, guided along the guide shafts 19, until the exchanging chuck 7 stops at the position E at which an upper carbon can be picked up.

(d) The moving cylinder lid is operated in a direction to extend the rod so that the guide wire 12a is loosened. The exchanging chuck assumes an open state wherein a carbon can be received thereby.

(e) The carbon supply means movement device 10 is actuated to move the platform 10a and the annular member 23 toward the exchanging chuck to position C to thereby move the upper carbon 1' into the exchanging chuck 7.

(f) The moving cylinder 11a is operated in the direction to retract the piston rod so the guide wire 12a is tightened, and thus the exchanging chuck is closed to grip the upper carbon 1' therein.

(g) The carbon drive system moving unit 15 is operated to move the upper and lower carbon chucks from a carbon discharge position A to a carbon replacement position B.

(h) The carbon replacing system reversible motor 16 is actuated to move the exchanging chuck 7 holding the upper carbon 1' upward and stop it at the upper carbon mounting position F, and the carbon supply means 8 is retracted to its initial position D by operation of the moving means 10.

(i) The moving cylinder 11b of the chuck opening and closing system 13b is actuated to extend the piston rod so that the guide wire 12b is loosened and the upper carbon chuck 3 is opened.

(j) The carbon drive system moving unit 15 is actuated to move the upper and lower carbon chucks from the carbon replacement position B to the carbon discharge position A, in which the open upper carbon chuck moves around the carbon 1'.

(k) The moving cylinder 11b is actuated to retract the piston rod so that the guide wire 12b is tightened and the upper carbon chuck is closed to grip the upper carbon 1'.

(l) The moving cylinder 11a is actuated to extend the piston rod so that the guide wire 12a is loosened and the exchanging chuck 7 is opened to release the upper carbon 1'.

(m) The upper and lower carbon chucks are moved to the carbon replacement position B by the operation of the carbon drive shaft moving unit 15.

(n) The carbon replacing reversible motor 16 is operated to move the exchanging chuck downward and stop it at the carbon pickup position E.

(o) The carbon supply means 8 is actuated to move the lower carbon 2' to the position N opposite to the exchanging chuck 7.

(p) The carbon supply means movement device 10 is actuated to move the carbon supply means to the position C toward the exchanging chuck 7 and move the lower carbon 2' into the exchanging chuck 7.

(q) The piston moving cylinder 11a is retracted so that the guide wire 12a is tightened and the exchanging chuck is closed to hold the lower carbon 2'.

(r) The carbon replacing reversible motor 16 is operated to move the exchanging chuck 7 holding the lower carbon 2' upward and stop it at the lower carbon mounting position G.

(s) The carbon drive system moving unit 15 is actuated to move the upper and lower carbon chucks 3 and 4 from the carbon replacement position B to the carbon discharge position A.

(t) The moving cylinder 11c of the chuck opening and closing system 13c is moved to retract the piston rod so that the guide wire 12c is tightened and the lower chuck 4 is closed to grip the lower carbon 2'.

(u) The moving cylinder 11a of the chuck opening and closing system 13a is actuated to extend the piston rod so that the guide wire 12a is loosened and the exchanging chuck 7 is opened to release the lower carbon 2'. Each of the upper and lower carbon chucks now holds a corresponding carbon.

(v) The carbon drive system moving unit 15 is actuated to move the upper and lower carbon chucks from the carbon discharge position A to the carbon replacement position B.

(w) The carbon replacing reversible motor 16 is actuated to move the exchanging chuck 7 downward and stop it at the carbon pickup position E.

(x) The carbon drive system moving unit 15 is actuated to move the upper and lower carbon chucks to the carbon discharge position A.

(y) The reversible motor 5 is actuated to turn the driving screw 20a of the carbon drive system 6 in a direction to bring the upper and lower carbons into contact with each other to start discharge.

The distance between the ends of the upper and lower carbons is adjusted by turning stopping the reversible motor 5 so that the discharge current remains at 60A.

The upper and lower carbons are consumed while continuously producing discharge.

(z) When the upper and lower carbons are consumed to the point where they are no longer suitable, the upper and lower carbon chucks 3 and 4 are stopped at the discharge end portions J and K, respectively.

(A) The upper and lower carbon chucks are moved to the carbon replacement position B.

(B) The carbon supply means is operated to move the used carbon holder which is between lower and upper replacement carbons to a position opposite the exchanging chuck 7.

(C) The exchanging chuck 7 is moved upward by the carbon replacing system and stopped at the upper carbon removing position H.

(D) The carbon drive system moving unit 15 is actuated to move the upper and lower carbon chucks 3 and 4 to the carbon discharge position A to move the upper consumed carbon into the exchanging chuck 7.

(E) The moving cylinder 11a of the chuck opening and closing system 13a is actuated to retract the piston rod so that the guide wire 12a is tightened and the exchanging chuck is closed to grip the consumed upper carbon 3.

(F) The moving cylinder 11b of the chuck opening and closing system 13b is actuated to extend the piston rod so that the guide wire 12b is loosened and the upper carbon chuck 3 is opened to release the consumed upper carbon.

(G) The carbon drive system moving unit 15 is actuated to move the upper and lower carbon chucks 3 and 4 to the carbon replacement position B.

(H) The exchanging chuck is moved downward by the operation of the carbon replacing system and stopped at the position E.

(I) The carbon supply means movement device 10 is actuated to move the member 23 to the position C with the used carbon holder to a position just under the consumed upper carbon.

(J) The moving cylinder 11a is operated to extend the piston rod so that the guide wire 12a is loosened and the exchanging chuck is opened to release the consumed upper carbon so that it is received in the used carbon holder.

(K) The consumed carbon is replaced by a new one by a sequence of steps (b), (e), (f), (h), (j), (k), (l), (m), and (n).

(L) The carbon supply means is actuated to move the next empty used carbon holder between an upper and a lower carbon to the position opposite to the exchanging chuck 7.

(M) The exchanging chuck 7 is moved upward by the carbon replacing system and stopped at the lower carbon removing position I.

(N) The carbon drive system moving unit 15 is actuated to move the upper and lower carbon chucks to the carbon discharge position A, thus moving the lower consumed carbon into the exchanging chuck 7.

(O) The moving cylinder 11a of the chuck opening and closing system 13a is actuated to retract the piston rod so that the guide wire 12a is tightened and the exchanging chuck 7 is closed to grip the lower consumed carbon.

(P) The moving cylinder 11c of the chuck opening and closing system 13c is actuated to extend the piston rod so that the guide wire 12c is loosened and the lower carbon chuck 4 is opened to release the lower consumed carbon.

(Q) The carbon drive system moving unit 15 is actuated to move the upper and lower carbon chucks to the carbon replacement position B.

(R) The exchanging chuck 7 is moved downward by the carbon replacing system and stopped at the position E.

(S) The carbon supply system movement device 10 is operated to move the member 23 in the direction of the exchanging chuck to the position C and move the used carbon holder to a position just under the lower consumed carbon.

(T) The moving cylinder 11c is actuated to extend the piston rod so that the guide wire 12c is loosened and the exchanging chuck is opened to release the lower consumed carbon, the consumed carbon thus being received in the used carbon holder.

(U) The consumed lower carbon is replaced by a new one through a sequence of steps (o), (p), (q), (r), (s), (t), (u), (v), (w), and (x).

The carbon drive system reversible motor 5 is then actuated so that the upper and lower carbon chucks are brought closer to each other by the carbon drive system 6 and discharge is started between the upper and lower carbons. Thus, the same operation as in the step (y) is performed.

The above-described sequence of operation instructions in steps (a) through (U) are generated from the electrical control system.

With a conventional weather resistance testing apparatus using carbon arc lamps, the maximum time span during which a carbon arc lamp can be lighted is 60 hours, and therefore the carbons must be replaced every 60 hours. However, a test may require as long as 2000 or 3000 hours. Even if such a test is interrupted only while a carbon is being replaced so that the weather resistance testing apparatus is operated with efficiency, the time needed for replacing the carbons sometimes falls in the night or on a holiday thus placing a heavy burden on the operator. Since with the present invention the operator only has to supply carbons to the carbon supply means and the carbons are automatically replaced, the operator is relieved of the burden of the carbon exchanging tasks. Moreover, because it is unnecessary to wait for the consumed carbons to cool, because they are handled by the chuck 7, the time required for the work can be reduced to 1/20 of the conventional time or less, which means a large reduction in labor costs.

What is claimed is:

1. In a carbon-arc weather resistance testing apparatus having a carbon drive system including a reversible motor for automatically moving upper and lower arc producing carbons toward and away from each other along a vertical line for keeping the discharge current and voltage substantially constant, the improvement comprising:

a carbon exchanging system having:
remotely operable upper and lower carbon chucks for holding the upper and lower carbons;
a carbon replacing means having a remotely operable exchanging chuck and means for moving said exchanging chuck along a path of movement toward and away from the upper and lower carbon chucks when they are in position on the vertical line;
means for shifting said carbon drive system and said carbon replacing means relative to each other for moving the upper and lower chucks and said exchanging chuck laterally relative to the vertical line;
a carbon supply means adjacent the path of movement of said exchanging chuck for holding replacement carbons and moving them into position opposite a position of said exchanging chuck along said path; and means for moving said exchanging chuck and said carbon supply means relative to each other in a direction toward and away from each other.

2. The improvement as claimed in claim 1 in which said upper and lower chucks and said exchanging chuck include fluid operated piston cyinder means and guide wire means extending from said piston cylinder means to said chucks for remotely operating said chucks.

3. The improvement as claimed in claim 1 in which said shifting means comprises means for shifting said carbon drive system laterally relative to the vertical line.

4. The improvement as claimed in claim 1 in which said means for moving said exchanging chuck and said carbon supply means relative to each other comprises means for moving said carbon supply means toward and away from the position of said exchanging chuck opposite said carbon supply means.

5. The improvement as claimed in claim 4 in which said carbon replacing means comprises means for moving said exchanging chuck along the vertical line, and said carbon supply means is adjacent the lower end of the vertical line.

6. The improvement as claimed in claim 4 in which said carbon supply means comprises an annular ring having replacement carbon holders thereon for holding replacement carbons in a position for being gripped by said exchanging chuck when said carbon supply means is moved toward said exchanging chuck.

7. The improvement as claimed in claim 4 in which said carbon supply means comprises an endless chain having replacement carbon holders thereon for holding replacement carbons in a position for being gripped by said exchanging chuck when said carbon supply means is moved toward said exchanging chuck.

8. The improvement as claimed in claim 4 in which said carbon supply means comprises a closed figure member having replacement carbon holders thereon for holding replacement carbons in a position for being gripped by said exchanging chuck when said carbon supply means is moved toward said exchanging chuck, and further having consumed carbon receiving holders between each pair of replacement carbon holders for receiving consumed carbons from said exchanging chuck.

9. The improvement as claimed in claim 1 further comprising a control system connected to said upper and lower carbon chucks, said exchanging chuck and said means for moving said exchanging chuck, said shifting means, said carbon supply means and said carbon supply moving means for actuating the respective chucks and means for causing said upper and lower chucks to be shifted laterally relative to the vertical line, for causing said exchanging chuck to be moved into a position opposite one of the carbons, for causing said shifting means to shift the upper and lower chucks back to the position of the vertical line for inserting one of the carbons into the exchanging chuck, for causing the exchanging chuck to move to the position opposite the carbon supply means, for causing the carbon supply means to move a consumed carbon holder into position corresponding to a carbon in the exchanging chuck and pick up such a consumed carbon, for causing the carbon supply means to feed a replacement carbon into position opposite the exchanging chuck and then move the replacement carbon into the exchanging chuck, and then for causing the exchanging chuck to move back to a position corresponding to an upper or lower carbon chuck and deliver a replacement carbon thereto.

* * * * *